United States Patent [19]

Senin et al.

[11] Patent Number: 4,642,340

[45] Date of Patent: Feb. 10, 1987

[54] STABLE COMPOUNDS OF GLUCOSAMINE SULPHATE

[75] Inventors: Paolo Senin; Francesco Makovec, both of Monza; Luigi Rovati, San Fruttuoso di Monza, all of Italy

[73] Assignee: Rotta Research Laboratorium S.p.A., Milan, Italy

[21] Appl. No.: 373,542

[22] Filed: Apr. 30, 1982

[30] Foreign Application Priority Data

Apr. 30, 1981 [IT] Italy ................................ 67596 A/81

[51] Int. Cl.$^4$ .............................................. C07H 5/06
[52] U.S. Cl. .................................................. 536/55.2
[58] Field of Search .................. 536/55.2, 52; 424/180; 514/53

[56] References Cited

U.S. PATENT DOCUMENTS 3,232,836  1/1966  Carlozzi et al. .................. 424/180
3,683,076  8/1972  Rovati ............................... 424/180

FOREIGN PATENT DOCUMENTS 1056331  1/1967  United Kingdom .............. 536/111

*Primary Examiner*—Albert T. Meyers
*Assistant Examiner*—C. Joseph Faraci
*Attorney, Agent, or Firm*—Sughrue, Mion, Zinn, Macpeak, and Seas

[57] ABSTRACT

The compound consists of a mixed salt of glucosamine sulphate and sodium chloride corresponding to the formula:

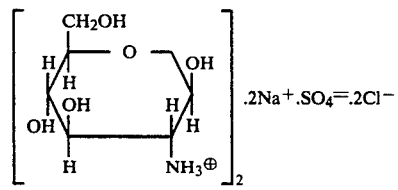

and is in the form of a crystalline powder with a melting point above 300° C. The salt is stable at ambient temperatures and humidities and has pharmacological properties practically identical to those of glucosamine sulphate.

5 Claims, No Drawings

STABLE COMPOUNDS OF GLUCOSAMINE SULPHATE

The subject of the present invention is a mixed salt of glucosamine sulphate and sodium chloride, a process for preparing this salt and the use of the said salt in the preparation of pharmaceutical forms otherwise unobtainable, or difficult to obtain, from glucoseamine sulphate.

Glucosamine sulphate is a well known and extremely important substance in the treatment of rheumatic fever, arthritic and arthrosic complaints, both in the acute and chronic forms, and, generally, of all pathological conditions originating from metabolic disorders of the osteo-articular tissue.

The synthesis of glucosamine sulphate was described by Breuer in 1898 (Chem. Ber. 31, 2197) and an industrial method is the subject of U.K. Pat. No. 1056331, U.S. Pat. No. 3,683,076 and Swiss Pat. No. 525,861, all owned by our Company.

However, until now, it has not been possible to eliminate several unfavourable properties of this compound, specifically, its highly hygroscopic nature and the facility with which its amino group oxidises if not completely saltified.

These unfavourable properties give rise to difficulties and limitations in the practical use of glucosamine sulphate. For example, oral forms, such as tablets or capsules, require anti-oxidants, such as sodium hyposulphite, to be present in their formulations, which substances, although blocking the oxidation of the amino group, leave the problem of the hygroscopic nature of the sulphate unsolved; this necessitates the preparation of these forms in environments with a relative humidity not greater than 30%, with results which are even then unsatisfactory and with a stability lifetime which is practically insufficient for their use. Similar comments apply to rectal forms (suppositories) which, even if kept under dry, refrigerated conditions, degrade with considerable rapidity.

There remain the injectable forms, which are rather delicate to prepare but which are sufficiently stable for practical purposes. It is not possible to make freeze-dried preparations since, invariably, products having the appearance and consistency of viscous oils are obtained, which are thus practically unusable.

It has now been found that it is possible to stabilise glucosamine sulphate by the formation of a mixed salt thereof with sodium chloride. This result is certainly surprising in that it was not predictable that a hygroscopic salt, such as glucosamine sulphate, might be stabilised by sodium chloride, which is another hygroscopic salt.

The mixed salt which is the subject of the present invention and which will be called "glucosamine-SP" for brevity, is constituted by an ionic lattice in which the cations are constituted by protonated glucosamine and $Na^+$, and the anions are $Cl^-$ and $SO_4^=$, these cations and anions being distributed in a fashion such that the simplest formula is $2\ (C_6H_{14}NO_5)^+.Na^+.SO_4^=.2Cl^-$ and the structural formula is:

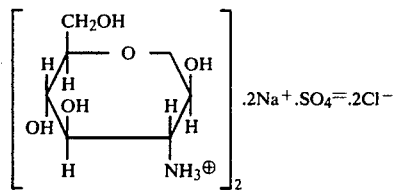

Its melting point is above 300° C. and its sensitivity to ambient relative humidity, even at high temperatures (as will be seen below) is practically negligible.

The method of preparation of glucosamine-SP comprises essentially the steps of: dissolving dry particular sodium chloride under agitation in a quantity of distilled water which may vary between 5.5 and 7.5 (preferably 6.5) times the weight of the sodium chloride itself, at a temperature of from 50° C. to 70° C. (preferably 60° C.); dissolving in the obtained solution the stoichiometric quantity of glucosamine sulphate at a solution temperature of from 35° C. to 45° C. (preferably 40° C.), under agitation; precipitating glucosamine-SP by the addition of a liquid precipitant which is miscible with water and in which glucosamine-SP has a solubility not greater than 0.1% (weight/volume), while operating under agitation at a temperature of from 40° C. to 50° C. (preferably at 45° C.); completing the precipitation at a lowered temperature; and recovering the precipitated glucosamine-SP.

The liquid precipitants which may be used are, for example, acetone, ethanol, acetonitrile, tetrahydrofuran and dioxan, and are preferably added in volumes of 5 to 7 (preferably 6) times the volume of the distilled water used for dissolving the starting salts. To advantage, the addition of the liquid precipitant is carried out over a period of 2.5 to 3.5 (preferably 3) hours, whereupon the resulting suspension of glucosamine-SP is maintained for a further period, variable between 12 and 24 (preferably 18) hours, under slow agitation, and at a temperature of from 25° C. to 35° C. (preferably 30° C.) in order to allow both the complete precipitation and the correct growth of the crystals. Once the necessary time has elapsed, the reaction mass is further cooled to a temperature of from 0° C. to 10° C. (preferably 5° C.) and the glucosamine-SP crystals are filtered off and dried in an oven with air circulation, for example at a temperature of from 45° C. to 65° C. (preferably 55° C.) for a period of time which may very from 12 to 24 (preferably 18) hours.

The glucosamine sulphate which is used with the sodium chloride in the synthesis may be prepared substantially as described in Swiss Pat. No. 525,861, by liberation of the glucosamine from its hydrochloride in an aqueous-alcoholic medium, in the presence of triethylamine, and subsequent treatment of the obtained base in an acetone medium with the stoichiometric quantity of concentrated sulphuric acid to give the glucosamine sulphate. In the patent cited above ethyl ether is used but, in industrial preparations on a large scale, it is preferred to use acetone which is much less dangerous and, moreover, yields a product with the same characteristics as those described in said patent.

EXAMPLE 1

Preparation of glucosamine-SP using acetone as the precipitating agent 75 ml distilled water are loaded into a four-necked flask of a useful volume of 750 ml, provided with a paddle stirrer, a thermometer and a condenser and the flask is heated to a temperature of 60° C. in an electrically-heated bath. 11.68 g (0.2 mol.—M.W. 58.4) of sodium chloride, previously dried to constant weight in an oven at 70° C., are added with moderate stirring (170±10 revolutions per minute) and the mass is maintained under agitation at 60° C. until the solid has completely dissolved, which takes about 20 minutes. As a general rule, the stirring should be carried out so as to avoid both the deposition of particles on the bottom of the flask and their projection against the walls, since, in either case, the dissolution would become more difficult.

Once the solid has completely dissolved, the temperature is lowered to 40° C. and 45.64 g (0.1 moles—M.W. 456.4) of glucosamine sulphate (previously prepared and maintained in an environment with a relative humidity not greater than 30% and a temperature not above 15° C.) is added, the temperature and the stirring at 170±10 revolutions per minute being maintained for the reasons specified above. During this stage a temperature above 45° C. could result in the product turning yellow while at a temperature below 35° C. The glucosamine sulphate would dissolve too slowly for practical purposes.

Under the recommended conditions, the sulphate dissolves completely in about 45 minutes, whereupon the temperature is brought to 45° C. and the precipitation is effected. At temperatures below 45° C. precipitation occurs too quickly, with formation of crystalline agglomerates which may encapsulate some solvent and impurities, while above 50° C. an undesirable yellowing of the suspension may occur. The precipitation is carried out by using 450 ml of acetone, which is added dropwise over a period of 3 hours. In less than 2.5 hours the precipitation occurs too rapidly, while a time of more than 3.5 hours offers no practical advantages. Stirring at 140±10 revolutions per minute is effected during precipitation, ensuring a correct balance between homogenisation of the phases and formation of the optimum quantity of nuclei for crystallisation.

Once the addition of the precipitating agent is terminated, the precipitation is completed and the preciptate is conditioned by lowering the temperature to 30° C. and reducing the stirring rate to 100±10 revolutions per minute for a period of 18 hours. Under these conditions a product with a high purity is obtained since the temperature of 30° C. in the conditioning stage favours the expulsion of any impurities and the reorganisation of the crystals, with absorption of any ions remaining in solution, while the mild agitation allows the whole precipitated mass to be maintained constantly in contact with the solution without altering the uniformity of the crystalline mass. The time indicated above is that necessary to allow the completion of the processes described above. After 18 hours, the temperature is lowered to 5° C. with the aid of an ice-water bath and the crystalline mass obtained is filtered through a Buchner funnel.

After the mass has been well squeezed in order to remove the greatest possible quantity of mother-liquid, it is transferred to an oven with air circulation and dried at 55° C. for 18 hours.

50.5 g (yield 88.1%) of creamy white crystals with a bitter taste are obtained.

The glucosamine-SP thus prepared has the following characteristics:

| Microanalysis for $C_{12}H_{28}Cl_2N_2Na_2SO_{14}$: | | |
|---|---|---|
| | theoretical % | % found |
| carbon | 25.14 | 25.02 |
| hydrogen | 4.92 | 4.70 |
| nitrogen | 4.88 | 4.85 |
| Glucosamine titre | 97.5–102.5% (according to Elson L. A.-Morgan W. T. J.: Biochem. J., 27, 1824, (1933)). | |
| Sulphate titre | 97.5–102.5% (by precipitation with $BaCl_2$ and titration with EDTA in a medium made basic with $NH_3$, in the presence of the indicator eriochrome black T - sodium rhodizonate 2:1). | |
| Chloride titre | 97.5–102.5% (argentometric method). | |
| Sodium titre | 97.5–102.5% (flame photometry). | |

Appearance, Colour, Smell: Crystalline powder, bright cream colour, no smell and with a very bitter taste.

Solubility (at 25° C.—w/v).

This test was carried out by preparing saturated solutions of glucosamine-SP in various solvents and determining the concentration of the glucosamine by the Elson-Morgan colorimetric method mentioned above.

Water: very soluble (~40%)
Methanol: slightly soluble (~1%)
Ethanol: very slightly soluble (~0.03%)
Acetone, acetonitrile, tetrahydrofuran, dioxan: practically insoluble (<0.01%).
Benzene, chloroform, carbon tetrachloride, methylene chloride, ligroin, ethyl ether: insoluble.

pH-value:

The pH of an aqueous saturated solution of glucosamine-SP at 20° C. is 3.0±0.2.

Partition Coefficient (K): The partition coefficient K of glucosamine-Sp determined at 25° C. in a mixture of phosphate buffer (pH 6.8) with n-octanol has a value which tends to infinity.

Melting point: >300° C. (with partial decomposition above 200° C.).

Specific rotation: $[\alpha]_0^{20} = +52 \pm 0.1°$ (at equilibrium in 10% aqueous solution).

Weight loss in drying: $\leq 0.5\%$ (at 40° C./16–18 Torr for 8 hours in the presence of sulphur trioxide).

EXAMPLE 2

Preparation of glucosamine-SP using ethanol as the precipitating agent

The procedure is as described in Example 1, with the use of absolute ethanol instead of acetone. 48.9 g (yield 85.3%) of glucosamine-SP are obtained with the same characteristics as those described in Example 1.

EXAMPLE 3

Preparation of glucosamine-SP using acetonitrile as the precipitating agent

The procedure is as described in Example 1, with the use of acetonitrile instead of acetone. 51.2 g (yield 89.3%) of glucosamine-SP are obtained having the characteristics described in Example 1.

Example 4

Preparation of glucosamine-SP using tetra hydrofuran as the precipitating agent The procedure is as described in Example 1, with the use of tetrahydrofuran instead of acetone. 48.1 g (yield 83.9%) of glucosamine-SP are obtained having the characteristics described in Example 1.

EXAMPLE 5

Preparation of glucosamine-SP using dioxan as the precipitating agent

The procedure is as described in Example 1, with the use of dioxan instead of acetone. 47.6 g (yield 83.04%) of glucosamine-SP are obtained having the characteristics described in Example 1.

In order to make clear the difference in stability between the glucosamine-SP prepared by the method described above and glucosamine sulphate (prepared as described in the previously cited Switt Pat. No. 525,861), comparative stability tests were carried out under various conditions of temperature and relative humidity.

Two parameters were taken into consideration for the evaluation, that is, the external appearance of the tested substances and the percent titre of glucosamine determined by the previously cited Elson-Morgan colorimeric method.

The external appearance of the glucosamine sulphate was evaluated according to a scale of from 1 to 6, the significance of which is as follows:
1: Microcrystalline powder of white-cream colour
2: Slight yellowing with formation of some lumps
3: Marked yellowing with numerous darker lumps
4: Bright brown colouring and pasty consistency
5: Brown-coloured viscous paste
6: Dark brown liquid.

Such a scale resulted not necessary for the glucosamine-SP since its appearance remained the same in all the tests and accordingly the scale value assigned was always 1.

The results obtained are given in Tables 1 to 6.

TABLE 1

Stability of Glucosamine-SP and of Glucosamine sulphate at 15° C. and 30% R.H.

| Time (days) | Glucosamine sulphate Appearance | Titre | Glucosamine-SP Appearance | Titre |
|---|---|---|---|---|
| 0 | 1 | 98.7% | 1 | 101.2% |
| 7 | 1 | 99.3% | 1 | 100.7% |
| 15 | 1 | 98.4% | 1 | 101.5% |
| 30 | 1 | 99.3% | 1 | 101.1% |
| 60 | 1 | 98.1% | 1 | 100.4% |
| 120 | 2 | 97.2% | 1 | 101.9% |
| 360 | 2-3 | 84.1% | 1 | 100.7% |

TABLE 2

Stability of Glucosamine-SP and of Glucosamine sulphate at 15° C. and 45% R.H.

| Time (days) | Glucosamine sulphate Appearance | Titre | Glucosamine-SP Appearance | Titre |
|---|---|---|---|---|
| 0 | 1 | 99.5% | 1 | 100.7% |
| 7 | 1 | 98.3% | 1 | 99.1% |
| 15 | 1 | 100.2% | 1 | 99.8% |
| 30 | 1 | 99.4% | 1 | 100.4% |
| 60 | 2 | 86.2% | 1 | 98.6% |
| 120 | 4 | 42.9% | 1 | 99.1% |
| 360 | 6 | not deter. | 1 | 98.4% |

TABLE 3

Stability of Glucosamine-SP and of Glucosamine sulphate at 15° C. and 60% R.H.

| Time (days) | Glucosamine sulphate Appearance | Titre | Glucosamine-SP Appearance | Titre |
|---|---|---|---|---|
| 0 | 1 | 99.5% | 1 | 101.2% |
| 3 | 1 | 98.4% | 1 | 101.8% |
| 6 | 3 | 76.2% | 1 | 100.5% |
| 12 | 5 | 31.4% | 1 | 99.8% |
| 24 | 6 | not deter. | 1 | 99.5% |
| 36 | 6 | " | 1 | 101.3% |
| 48 | 6 | " | 1 | 100.7% |

TABLE 4

Stability of Glucosamine-SP and of Glucosamine sulphate at 25° C. and 30% R.H.

| Time (days) | Glucosamine sulphate Appearance | Titre | Glucosamine-SP Appearance | Titre |
|---|---|---|---|---|
| 0 | 1 | 99.6% | 1 | 99.1% |
| 7 | 1 | 99.1% | 1 | 99.7% |
| 15 | 1 | 98.3% | 1 | 98.5% |
| 30 | 1 | 99.5% | 1 | 99.9% |
| 60 | 2 | 87.8% | 1 | 100.4% |
| 120 | 3 | 75.2% | 1 | 98.2% |
| 360 | 4 | 40.4% | 1 | 99.9% |

TABLE 5

Stability of Glucosamine-SP and of Glucosamine sulphate at 25° C. and 45% R.H.

| Time (days) | Glucosamine sulphate Appearance | Titre | Glucosamine-SP Appearance | Titre |
|---|---|---|---|---|
| 0 | 1 | 100.5% | 1 | 98.9% |
| 3 | 1 | 100.3% | 1 | 99.5% |
| 6 | 1 | 99.8% | 1 | 98.6% |
| 12 | 2 | 90.3% | 1 | 97.7% |
| 24 | 3 | 74.5% | 1 | 98.1% |
| 36 | 5 | 29.6% | 1 | 97.7% |
| 48 | 6 | not deter. | 1 | 98.4% |

TABLE 6

Stability of Glucosamine-SP and of Glucosamine sulphate at 25° C. and 60% R.H.

| Time (hours) | Glucosamine sulphate Appearance | Titre | Glucosamine-SP Appearance | Titre |
|---|---|---|---|---|
| 0 | 1 | 99.3% | 1 | 100.7% |
| 2 | 1 | not deter. | 1 | not deter. |
| 4 | 1 | " | 1 | " |
| 8 | 2 | 95.8% | 1 | 101.2% |
| 16 | 3 | 73.8% | 1 | not deter. |
| 24 | 4 | 44.6% | 1 | 99.2% |
| 36 | 6 | not deter. | 1 | 100.4% |

From the results given in Tables 1 to 6 it is clear that glucosamine sulphate is a particularly unstable substance since it is readily oxidised and strongly hygroscopic. The conditions under which it is kept are clearly very important (particularly the ambient relative humidity) and must be rigorously controlled. Only at temperatures less than 15° C., with a relative humidity not greater than 30%, can a stability of about 4 to 5 months be obtained while at 25° C., under the same conditions of relative humidity, signs of degradation are shown even after about 60 days. Further, if the conditions of temperature and humidity are such as to be considered normal 25° C. and 60% R.H.) the first signs of degradation appear even after 4 hours and the glucosamine sulphate is completely decomposed after barely 36 hours.

Glucosamine-SP, on the contrary, shows to be particularly stable to temperature and humidity and hence is easy to preserve and perfectly usable in pharmaceutical techniques. From the tests described above it is seen that, after one year at 25° C. and a relative humidity of 60%, it is perfectly preserved and further tests have shown that, only by operating under extremely drastic conditions, that is at 40° C. and 85% relative humidity, is it possible to observe a slight darkening of the colour and a slight lowering of the glucosamine titre (about 3 to 4%) after about 12 months and this then remains constant under the same conditions of preservation for the subsequent 12 months.

PHARMACOTOXICOLOGICAL SECTION

Although there are marked differences in the physico-chemical characteristics, the stability and the conditions of preservation of glucosamine sulphate and glucosamine-SP, their pharmatoxicological properties are practically identical.

In confirmation of this, methods and results of testing the two substances contemporaneously "in vitro" and "in vivo" for their pharmacobiological activities, in addition to results of acute toxicity tests carried out on two animal species by different methods of administration are given below.

BIOLOGICAL ACTIVITY "IN VITRO"

Stimulation of the synthesis of glucosamino glucanes (GAG) in mice-embryo fibroblast cultures—evaluation carried out by uptale of $^{35}S$ Fibroblast are embryonic cells which, by successive differentiations, give rise to different types of the connective tissue and, consequently, of the osteo-cartilaginous tissue.

Such cells thus provide a very useful experimental model for the evaluation of any pharmabiological effects (both positive and negative) induced by substances under examination on tissues resulting from this cellular substrate, and particularly on articular tissue.

Methods and results of a test relating to the uptake of $^{35}S$ by sulphated mucopolysaccharides (GAG), mainly chondroitin-sulphate, both on the cellular and the extracellular level, wherein the uptake of $^{35}S$ is, consequently, proportional to the rate at which the GAG are synthesised by the fibroblasts, will now be given. For this purpose, primary cultures of mice-embryo fibroblasts (strain C57 BL/6 stCrl) were prepared by mechanical and enzymatic dissociation (in Trypsin Versene mixture-Microbiological Associates) of the embryos taken from the mother on the 18th day of pregnancy. The culture medium is the Eagle medium modified by Dulbecco and supplemented with 15% of calf foetus serum. The incubation atmosphere consists of 5% of carbon dioxide in air at 37° C. 24 hours after innoculation, the medium is replaced by a new medium containing the drug under examination and the radioactive precursor ($Na_2^{35}SO_4$) for the measurement of the synthesis both of soluble and tissue-bound GAG; the culture is left to incubate for a further 24 hours and then the culture medium (containing the soluble GAG) and fibroblasts (containing the tissue-bound GAG) are separated.

The soluble GAG are isolated from the culture medium by precipitation with a solution of 5% trichloroacetic acid in ice-water while the fibroblast residues, containing the tissue-bound GAG, after repeated washings with physiological solutions, are dissolved in DIMILUME or VERSENE.

The quantity of $^{35}S$ incorporated both in the soluble GAG and in the tissue-bound GAG are evaluated by the usual scintillation methods and expressed in cpm (counts per minute).

The tests were carried out five times for each sample in order to allow the results to be evaluated statistically.

The results obtained are given in Tables 7 and 8.

TABLE 7

Stimulation of the production of soluble GAG in mice-embryo fibroblast cultures. Evaluation by uptake of $^{35}S$

| SUBSTANCE | Conc. (γ/ml) | Soluble GAG synthesis (in cpm) Average ± s.e. | $t_1^{(1)}$ | $p_1^{(1)}$ | $t_2^{(2)}$ | $p_2^{(2)}$ | Δ % over n.t ct. |
|---|---|---|---|---|---|---|---|
| Untreated controls | — | 5830 ± 654 | — | — | — | | ±0 |
| Glucosamine sulphate | 10 | 7250 ± 905 | 1.27 | N.S. | — | | +24.3 |
| Glucosamine sulphate | 50 | 11430 ± 1108 | 4.35 | <0.01 | — | | +96.0 |
| Glucosamine sulphate | 100 | 9980 ± 1271 | 2.90 | <0.02 | — | | +71.2 |
| Glucosamine-SP | 12.5[(3)] | 6750 ± 718 | 0.95 | N.S. | 0.43 | N.S. | +15.8 |
| Glucosamine-SP | 62.5[(3)] | 12730 ± 1201 | 5.04 | <0.01 | 0.80 | N.S. | +118.3 |
| Glucosamine-SP | 125[(3)] | 12440 ± 1473 | 4.10 | <0.01 | 1.26 | N.S. | +113.3 |

TABLE 8

Stimulation of the production of tissue-bound GAG in mice-embryo fibroblast cultures. Evaluation by uptake of $^{35}S$

| SUBSTANCES | Conc. (γ/ml) | Soluble GAG Synthesis (in cpm) Average ± s.e. | $t_1^{(1)}$ | $p_1^{(1)}$ | $t_2^{(2)}$ | $p_2^{(2)}$ | Δ % over n.t. ct. |
|---|---|---|---|---|---|---|---|
| Untreated controls | — | 4680 ± 664 | — | — | — | — | ±0 |
| Glucosamine sulphate | 10 | 6210 ± 779 | 1.49 | N.S. | — | — | +32.7 |
| Glucosamine sulphate | 50 | 8220 ± 1003 | 2.94 | <0.02 | — | — | +75.6 |
| Glucosamine sulphate | 100 | 9110 ± 879 | 4.02 | <0.01 | | | +94.7 |
| Glucosamine-SP | 12.5[3] | 5490 ± 604 | 0.90 | N.S. | 0.73 | N.S. | +17.3 |
| Glucosamine-SP | 62.5[3] | 7780 ± 612 | 3.38 | <0.01 | 0.37 | N.S. | +66.2 |
| Glucosamine-SP | 125[3] | 8320 ± 1295 | 2.50 | <0.05 | 0.50 | N.S. | +77.8 |

Notes to Tables 7 and 8:

The statistical significance was evaluated by the Student "t" test.

Thus, the Student "t" values relating to the comparison between groups of values under consideration are given in the columns headed $t_1$ and $t_2$ while columns headed $p_1$ and $p_2$ report statistical probabilities that the compared groups of values belong to the same population.

Hence the notation N.S. indicates that the groups of values compared are not, from a statistical point of view, significantly different.

It is assumed, however, that two groups of values compared are statistically different when p, in dependence on the value "t" and the degrees of freedom, is 0.05.

(1): $t_1$ and $p_1$ relate to the comparison between treated groups and non-treated controls.

(2): $t_2$ and $p_2$ relate to the comparison between groups treated with equal doses, that is:

Glucosamine sulphate 10 γ/ml, glucosamine-SP 12.5 γ/ml, and so on.

(3): 12.5, 62.5 and 125 γ/ml of glucosamine sulphate.

Abbreviation meanings for Tables 7 and 8:

cpm: counts per minute
s.e.: standard error
n.t. ct: non-treated controls.

From the results given in Tables 7 and 8 it can be seen that glucosamine sulphate and glucosamine-SP, at the same concentrations, have the same activity in stimulating the synthesis of both soluble and tissue-bound GAG by mice-embryo fibroblasts.

PHARMOCOLOGICAL ACTIVITY "IN VIVO"

Anti-inflammatory activity in tests on granuloma induced by cotton-pellets

The test consists of evaluating the capacity of the substances under examination to inhibit the formation of granuloma following the subcutaneous implantation of extraneous bodies (in this case, cotton pellets).

40 female albino rats of the Sprague Dawley strain, having a weight of about 130 g, subdivided at random into 5 groups of 8 animals, were used.

One group of animals was used as a control. The other 4 groups were treated orally with 300 and 600 mg/kg doses of glucosamine sulphate and 375 and 750 mg/kg doses of glucosamine-SP (corresponding respectively to 300 and 600 mg/kg of glucosamine sulphate).

After the subcutaneous implant of 2 cotton pellets each having a weight of 20 mg into the dorsal region, the animals were administered daily, for 4 consecutive days, with the substances under examination in the doses given above.

At the end of the treatment, the granuloma were taken from the animals, which had been killed by prolonged anaesthesis with ether, and were dried in an oven at a temperature of 60° C. for 24 hours and were then weighed.

The results obtained are given in Table 9.

TABLE 9

Anti-inflammatory activity of glucosamine sulphate and glucosamine-SP in the test for granuloma from cotton pellets in rats.

| TREATMENT | Dose (mg/kg/os) | Average dry weight of the granuloma (average ± s.e.) | $t_1^{(1)}$ | $p_1^{(1)}$ | $t_2^{(2)}$ | $p_2^{(2)}$ | % Inhibition |
|---|---|---|---|---|---|---|---|
| Untreated controls | — | 154.2 ± 11.9 | — | — | — | — | ±0 |
| Glucosamine sulphate | 300 | 91.2 ± 10.8 | 3.92 | <0.01 | — | — | 40.9 |
| Glucosamine sulphate | 600 | 70.7 ± 7.9 | 5.84 | <0.01 | — | — | 54.1 |
| Glucosamine-SP | 375[3] | 94.6 ± 10.7 | 3.73 | <0.01 | 0.22 | N.S. | 38.7 |
| Glucosamine-SP | 750[3] | 64.8 ± 7.0 | 6.47 | <0.01 | 0.56 | N.S. | 58.0 |

Note to table 9:
The meanings of $t_1$ $p_1$ $t_2$ $p_2^{(1) (2)}$ are the same as those given for Tables 7 and 8.
[3] 375 and 750 mg/kg of glucosamine-SP correspond to 300 and 600 mg/kg of glucosamine sulphate, respectively.

Not to Table 9:

The meanings of $t_1 p_1 t_2 p_2$ (1) (2) are the same as those given for Tables 7 and 8.

(3): 375 and 750 mg/kg of glucosamine-SP correspond to 300 and 600 mg/kg of glucosamine sulphate, respectively.

From the results given in Table 9 it can be seen that glucosamine sulphate and glucosamine-SP also have the same pharmacological activity "in vivo".

More precisely, for the same dosage, the two substances are equivalent from a pharmacological point of view.

ACUTE TOXICITY

A. In mice:

Swiss NMRI mice having an average weight of 20±2 g, subdivided in groups of 10 animals (5 females and 5 males) were used for each dose and for each method of administration.

The methods of administration were: oral by means of gastric probe, intramuscular and endovenous into the caudal vein.

The observation time after administration was 10 days.

The doses used and results obtained are given in Table 10.

TABLE 10

Acute toxicity of glucosamine sulphate and glucosamine-SP in mice with various methods of administration.

| SUBSTANCE | Method of Administration | Max. dose administered (mg/kg) | % mortality | $DL_{50}$ (mg/kg) |
|---|---|---|---|---|
| Glucosamine sulphate | Oral | 5000 | 0 | >5000 |
| Glucosamine sulphate | Intramuscular | 3000 | 0 | >3000 |
| Glucosamine sulphate | Endovenous | 1500 | 0 | >1500 |
| Glucosamine-SP | Oral | 6250[1] | 0 | >6250 |
| Glucosamine-SP | Intramuscular | 3750[1] | 0 | >3750 |
| Glucosamine-SP | Endovenous | 1875[1] | 0 | >1875 |

[1]1875, 3750 and 6250 mg/kg of glucosamine-SP correspond to 1500, 3000 and 5000 mg/kg of glucosamine sulphate, respectively.

B. In rats

Sprague Dawley albino rats having an average weight of about 150 g, subdivided into groups of 10 animals (5 males and 5 females) were used for each dose and for each method of administration.

The methods of administration were: oral by means of a gastric probe, intramuscular and endovenous into the caudal vein.

The observation time after administration was 10 days.

The doses used and the results obtained are given in Table 11.

TABLE 11

Acute toxicity of glucosamine sulphate and glucosamine-SP in rats with different methods of administration.

| SUBSTANCE | Method of administration | Max. dose administered (mg/kg) | % mortality | $DL_{50}$ (mg/kg) |
|---|---|---|---|---|
| Glucosamine sulphate | Oral | 5000 | 0 | >5000 |
| Glucosamine sulphate | Intramuscular | 3000 | 0 | >3000 |
| Glucosamine sulphate | Endovenous | 1500 | 0 | >1500 |
| Glucosamine-SP | Oral | 6250[1] | 0 | >6250 |
| Glucosamine-SP | Intramuscular | 3750[1] | 0 | >3750 |
| Glucosamine-SP | Endovenous | 1875[1] | 0 | >1875 |

[1]1875, 3750 e 6250 mg/kg of glucosamine-SP correspond to 1500, 3000 and 5000 mg/kg of glucosamine sulphate, respectively.

As may be seen from Tables 10 and 11, even at levels of acute toxicity, no differences are found between glucosamine sulphate and glucosamine-SP. For all the methods of administration and all the species of animals tested, both have such a low toxicity that there is no mortality even with very high doses, so that it is difficult to establish exactly a precise $DL_{50}$.

The fact that glucosamine-SP has the same pharmacotoxicological and pharmacokinetic characteristics as glucosamine sulphate, it is clear that the former, thanks to its properties of stability and ease of preparation, represents a clear progress in the state of the art. Accordingly, a number of examples of formulations of pharmaceutical preparations containing glucosamine-SP will be given below. It should be noted that they differ from the formulations described in U.S. Pat. No. 3,863,076 for pharmaceutical forms containing glucosamine sulphate in that they do not include stabilising or preserving ingredients or anti-oxidants since they present no problems with regard to their preparation, preservation or stability.

PREPARATIONS OF PHARMACEUTICAL FORMS FOR ORAL ADMINISTRATION

1. Capsules:

| | |
|---|---|
| Glucosamine-SP | 314 mg |
| Maize starch | 60 mg |
| Lactose | 28.5 mg |
| Magnesium stearate | 5 mg |
| Talc | 2.5 mg |

The components are mixed until a homogeneous mixture is obtained, sieved through a 30-mesh sieve and filled into a capsule of gelatine.

Each capsule contains 410 mg of powder, corresponding to 314 mg of glucosamine-SP.

2. Tablets:

| | |
|---|---|
| Glucosamine-SP | 314 mg |
| Lactose | 42 mg |
| Polyvinyl pyrrolidone | 20 mg |
| Carboxymethyl cellulose sodium salt | 10 mg |
| Silicon dioxide | 5 mg |
| Magnesium stearate | 5 mg |
| Talc | 4 mg |

The glucosamine-SP, the polyvinyl pyrrolidone and the lactose are formed into a paste with 95% ethanol, the paste is dried at 45° C., granulated and sieved through a 20-mesh sieve. The other ingredients are added to the obtained granulate and mixed until the mixture is homogeneous.

The mixture is then compression-moulded to form tablets having a weight of 400 mg and containing 314 mg of glucosamine-SP.

3. Dragées:

| | |
|---|---|
| Glucosamine-SP | 314 mg |
| Maize starch | 50.4 mg |
| Polyvinyl pyrrolidone | 6.4 mg |
| Glyceryl monostearate | 12.8 mg |
| Methyl-cellulose | 3.6 mg |
| Stearic acid | 4 mg |
| Silicon dioxide | 0.8 mg |
| Saccharose | 65.3 mg |
| Talc | 90.9 mg |
| Calcium carbonate | 25 mg |
| Gum arabic | 4.3 mg |
| Magnesium stearate | 5.6 mg |
| Shellac | 16.7 mg |
| Castor oil | 0.35 mg |
| Titanium dioxide | 3.8 mg |
| White beeswax | 0.05 mg |

The glucosamine-SP, starch, polyvinyl pyrrolidone, glyceryl monostearate, methyl-cellulose, stearic acid and titanium dioxide are mixed until homogeneous, sieved through a 30-mesh sieve and compression-moulded to form cores of 392 mg. The prepared cores are coated, in an enrober, with a suspension of talc, magnesium stearate, shellac and castor oil in 95% ethanol and subsequently dried for 12 hours at 35° C.

Primary dragées of 415.7 mg are obtained which are further coated with a previously-prepared aqueous suspension containing the saccharose, talc, calcium carbonate, gum arabic and titanium dioxide. After drying at 30° to 35° C. for 12 hours, dragées of 603.95 mg are obtained which are finally polished with the beeswax.

The final weight of the dragées is 604 mg and the glucosamine-SP content is 314 mg.

PREPARATION OF PHARMACEUTICAL FORMS FOR RECTAL ADMINISTRATION

| | |
|---|---|
| Glucosamine-SP | 314 mg |
| Semi-synthetic glycerides | 1586 mg |
| Polysorbitan monostearate | 80 mg |
| Distilled H$_2$O | 20 mg |

The semi-synthetic glycerides are melted at 45° C. under constant agitation; still under agitation, a previously-prepared mixture of water and polysorbitan monostearate is added and finally the glucosamine-SP, which has previously been micronized to a grain size of from 5 to 20 microns, is added.

The mixture is left under agitation for 30 minutes, that is until complete dispersion is achieved, then it is injected into polyvinylchloride shells which, after cooling, are sealed.

Suppositories weighing 2000 mg, containing 314 mg of glucosamine-SP are obtained.

PREPARATIONS OF PHARMACEUTICAL FORMS WHICH CAN BE USED FOR INTRAMUSCULAR, INTRAVENOUS, INTRA-ARTICULAR INJECTIONS

1. Phials:

| | |
|---|---|
| Phial A: | |
| Glucosamine-SP | 502.5 mg |
| Lidocaine hydrochloride | 10 mg |
| H$_2$O for injection to make | 2 ml |
| Phial B: | |
| Diethanolamine | 24 mg |
| H$_2$O for injection to make | 1 ml |

PREPARATION OF PHIAL A

The glucosamine-SP and the lidocaine hydrochloride are dissolved in water in the proportions indicated, under agitation, filtered under inert gas blanket through a membrane filter with a porosity of 0,45, and introduced into 3 ml phials which are finally sterilised at 115° to 120° C. for 30 minutes in an autoclave with a steam current.

PREPARATION OF PHIAL B

The diethanolamine is dissolved in water under agitation in the proportion indicated, filtered under inert gas blanket through a membrane filter with a porosity of 0,45, introduced into 1 ml phials which are finally sterilised at 115° to 120° C. for 30 minutes in an autoclave with a steam current.

Pairs of 3 ml and 1 ml phials are obtained, the contents of which are mixed immediately before use. This recourse is due to the fact that the natural pH of glucosamine-SP, at the concentrations used, is about 3 and therefore is physiologically unacceptable.

In order to achieve a physiologically tolerable pH it is necessary to add a base (such as diethanolamine) with consequent liberation of the amino group of the glucosamine which, as stated above, is readily decomposable. Thus, for reasons of stability, use is made of pairs of phials, the contents of which are mixed immediately before use, with the double advantage of having a product which is stable with time (phial A), and which, by the addition of the base (phial B), achieves a physiological, and thus tolerable, pH.

2. Freeze-dried preparation

| | |
|---|---|
| Glucosamine-SP | 502.5 mg |
| Lidocaine hydrochloride | 10 mg |
| Diethanolamine | 20 mg |

The components are dissolved in the desired volume of sterile water for injections, filtered under an inert gas blanket through a membrane filter with a porosity of 0.45μ and freeze-dried in small flasks. A white solid residue is obtained which, in use, is dissolved in 2 ml of sterile water for injections within a time of not more than 30 seconds (pH 6.8).

We claim:
1. Mixed salt of glucosamine sulphate and sodium chloride corresponding to the formula:

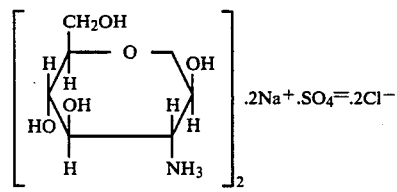

said mixed salt being in the form of a crystalline powder having a melting point above 300° C.

2. Process for the preparation of the mixed salt of glucosamine sulphate and sodium chloride according to claim 1, characterised by the steps of:
  (a) dissolving dry sodium chloride in 5.5 to 7.5 parts by weight of distilled water for every part of sodium chloride at a temperature of from 50° to 70° C. under agitation;
  (b) dissolving in the solution obtained in step (a) the stoichiometric quantity of glucosamine sulphate at a temperature of from 35° to 45° C., under agitation;
  (c) precipitating the mixed salt by the addition of a liquid precipitant which is miscible with water and in which the said mixed salt has a solubility not greater than 0.1% (w/v) while operating under agitation at a temperature of from 40° C. to 50° C.;
  (d) completing the precipitation by lowering the temperature of the mixture; and
  (e) recovering the precipitated mixed salt.

3. The process of claim 2, wherein the liquid precipitant is acetone, ethanol, acetonitrile, tetrahydrofuran or dioxan.

4. The process of claim 2 or 3, wherein the liquid precipitant is added in a proportion of 5 to 7 parts by volume with respect to the water used in step (a) over a period of from 2.5 to 3.5 hours.

5. The process of claim 2 or 3, wherein the recovered mixed salt is dried in air-circulation oven at 45°–65° C.

* * * * *